(12) United States Patent
Wall et al.

(10) Patent No.: US 9,788,720 B2
(45) Date of Patent: Oct. 17, 2017

(54) RETINAL IMAGING APPARATUS AND METHOD

(75) Inventors: Robert Wall, Fife (GB); Dan Gray, Fife (GB)

(73) Assignee: OPTOS PLC, Dunfermline, Fife (GB)

( * ) Notice: Subject to any disclaimer, the term of this patent is extended or adjusted under 35 U.S.C. 154(b) by 331 days.

(21) Appl. No.: 13/805,599

(22) PCT Filed: Jun. 2, 2011

(86) PCT No.: PCT/GB2011/051037
§ 371 (c)(1),
(2), (4) Date: Feb. 4, 2013

(87) PCT Pub. No.: WO2012/001381
PCT Pub. Date: Jan. 5, 2012

(65) Prior Publication Data
US 2013/0128225 A1     May 23, 2013

(30) Foreign Application Priority Data
Jul. 1, 2010    (GB) .................................. 1011096.3

(51) Int. Cl.
*A61B 3/14*      (2006.01)
*A61B 3/12*      (2006.01)
(Continued)

(52) U.S. Cl.
CPC ................. *A61B 3/14* (2013.01); *A61B 3/12* (2013.01); *G02B 17/008* (2013.01); *G02B 26/105* (2013.01)

(58) Field of Classification Search
CPC ..................................... A61B 3/12; A61B 3/14
(Continued)

(56) References Cited

U.S. PATENT DOCUMENTS 4,213,678 A    7/1980   Pomerantzeff et al.
4,365,874 A    12/1982  Milburn et al.
(Continued)

FOREIGN PATENT DOCUMENTS

CN        101489468 A     7/2009
CN        101534701 A     9/2009
(Continued)

OTHER PUBLICATIONS

Search Report for CN201180032906.6 issued Jul. 21, 2014.
Notification of Reasons for Refusal issued for JP 2013517524 dated May 26, 2015.

*Primary Examiner* — Zachary Wilkes
(74) *Attorney, Agent, or Firm* — Christopher J. McKenna; Shabbi S. Khan; Foley & Lardner LLP

(57) ABSTRACT

The invention provides an apparatus and method for illuminating, imaging and treating the retina of an eye. The apparatus (10) comprises an illuminating device (16) including a planar light source capable of producing light in a plane, such that the illuminating device (16) is capable of illuminating a circumferential line on the retina (12) and a support structure, wherein the illuminating device (16) is pivotably mountable to the support structure and is rotatable about an axis (18) which lies substantially on the plane defined by the light source, such that, in use, the illuminating device (16) may be rotated about the axis (18) to illuminate an area of the retina (12).

24 Claims, 5 Drawing Sheets

(51) Int. Cl.
*G02B 26/10* (2006.01)
*G02B 17/00* (2006.01)

(58) Field of Classification Search
USPC .......................................... 351/205, 245, 246
See application file for complete search history.

(56) References Cited

U.S. PATENT DOCUMENTS

| | | | |
|---|---|---|---|
| 6,337,920 B1 * | 1/2002 | Muhlhoff | .................. 351/200 |
| 7,637,617 B2 * | 12/2009 | Liu | ................ G02B 17/06 |
| | | | 351/221 |
| 2002/0159621 A1 | 10/2002 | Callies et al. | |
| 2004/0135971 A1 | 7/2004 | Ulbers | |
| 2007/0024965 A1 | 2/2007 | Sander | |
| 2008/0151185 A1 * | 6/2008 | Saito et al. | .................. 351/206 |

FOREIGN PATENT DOCUMENTS

| | | |
|---|---|---|
| DE | 202008013344 U1 | 12/2008 |
| GB | 1454675 A | 11/1976 |
| GB | 2440163 A | 1/2008 |
| JP | H11-123178 A | 5/1999 |
| JP | 2005-507727 A | 3/2005 |

* cited by examiner

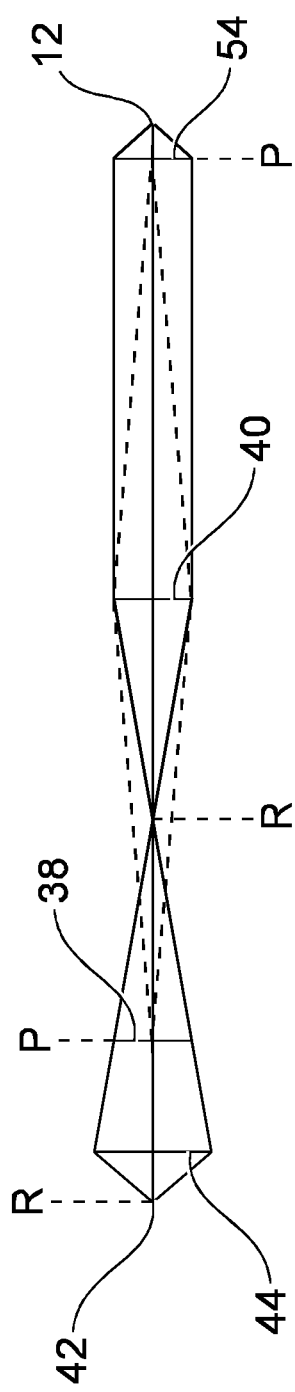
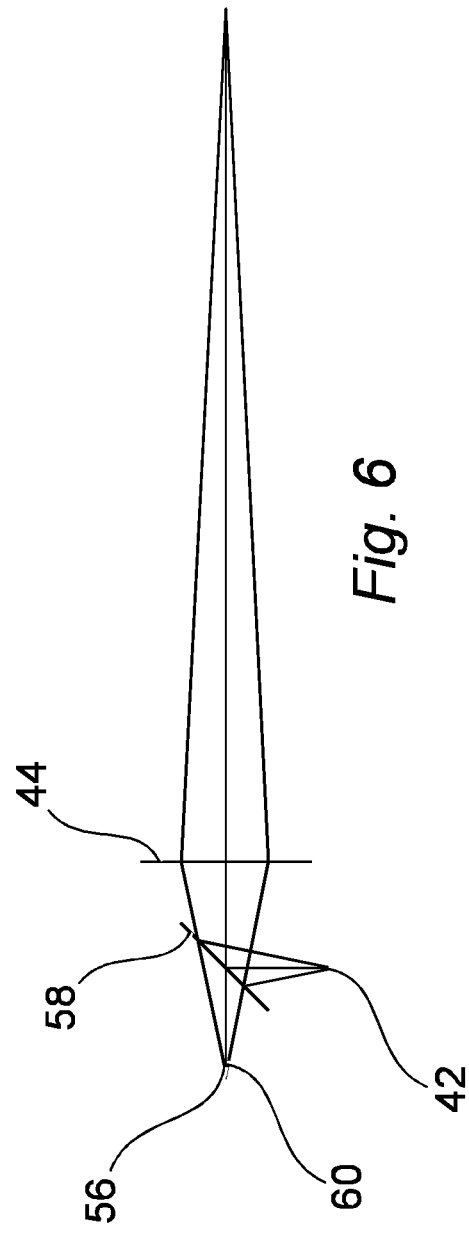

RETINAL IMAGING APPARATUS AND METHOD

The present invention relates to an apparatus and method for illuminating, imaging and treating the retina of a human eye.

Imaging systems, such as scanning laser ophthalmoscopes (SLOs), may comprise a large number of optical components, such as laser scanning elements, scan transfer mirrors, laser sources and detectors. The laser scanning arrangement consists of first and second orthogonal scanning elements, which typically include a high speed rotating polygonal mirror and a motor driven slow speed mirror. These elements are used to create a raster scan pattern of the human retina. The polygon mirror has a plurality of facets and typically provides the vertical scanning of the laser beam, and the slow speed mirror typically provides the horizontal scanning of the laser beam. The scan transfer mirror transfers the two dimensional laser scan pattern created by the scanning elements to the retina of the eye.

While such imaging systems provide acceptable images of the retina of the eye, they are limited in that they are expensive to manufacture (the laser scanning elements and scan transfer mirror are particularly expensive components), large in size and, due to the large number of optical components, have low optical efficiency.

According to a first aspect of the present invention there is provided an apparatus for illuminating the retina of an eye comprising:
  an illuminating device including a planar light source capable of producing light in a plane, such that the illuminating device is capable of illuminating a circumferential line on the retina; and
  a support structure;
  wherein the illuminating device is pivotably mountable to the support structure and is rotatable about an axis which lies substantially on the plane defined by the light source, such that, in use, the illuminating device may be rotated about the axis to illuminate an area of the retina.

The axis of rotation of the illuminating device may be located around the pupillary point of the eye. The axis of rotation of the illuminating device may be coincident with the front nodal point of the eye.

The axis of rotation of the illuminating device may lie on a horizontal plane defined by the optical axis of the eye. Alternatively, the axis of rotation of the illuminating device may be perpendicular to the horizontal plane defined by the optical axis of the eye. Alternatively, the axis of rotation of the illuminating device may not be parallel or perpendicular to the horizontal plane defined by the optical axis of the eye. In all of these arrangements, the axis of rotation of the illuminating device should lie on the plane defined by the light source.

The illuminating device may be configured such that its rotation about the axis is automated. The rotation of the imaging device may be computer-controlled.

The illuminating device may be configured to illuminate the retina by scanning collimated light across the retina of the eye. The illuminating device may therefore be capable of performing a one-dimensional scan of collimated light across the retina of the eye.

The axis of rotation of the illuminating device may be parallel to a plane defined by the one-dimensional collimated light scan produced by the illuminating device. That is, the plane of the axis of rotation of the illuminating device may be orthogonal to the plane defined by the one-dimensional collimated light scan it creates.

The rotational axis of the illuminating device may lie on the plane defined by the one-dimensional collimated light scan produced by the illuminating device.

The illuminating device may comprise:
  a source of collimated light; and
  a scanning element,
wherein the source of collimated light and the scanning element combine to provide a one-dimensional collimated light scan from a point; and
  the illuminating device further comprises a scan transfer device, wherein the scan transfer device has two foci and the point is provided at a first focus of the scan transfer device and the pupillary point of the eye is accommodated at a second focus of the scan transfer device, and wherein the scan transfer device transfers the one-dimensional collimated light scan from the point into the eye.

The front nodal point of the eye may be accommodated at the second focus of the scan transfer device.

The scanning element may be an oscillating mechanism.
The scanning element may be an oscillating mirror, such as an oscillating plane mirror.
The scanning element may be a resonant scanner.
The scanning element may be a resonant mirror, such as a resonant scanning mirror.
The scanning element may be a microelectromechanical system (MEMS) scanning element. The MEMS scanning element may be a one-dimensional scanning element or a two-dimensional scanning element.

The scan transfer device may comprise a tilted spherical mirror, an aspherical mirror, an elliptical mirror, an ellipsoidal mirror, a pair of parabola mirrors, a pair of paraboloidal mirrors or a lens system. In the case where the scan transfer device comprises a lens system, the lens system is arranged to provide two foci.

The source of collimated light may be a laser, a light emitting diode (LED), a Vertical Cavity Surface Emitting Laser (VCSEL), a super luminescent diode, a diode laser or a collimated incandescent lamp.

The source of collimated light may include one or more light sources. The source of collimated light may include one or more lasers, light emitting diodes (LEDs), Vertical Cavity Surface Emitting Lasers (VCSELs), super luminescent diodes, diode lasers or collimated incandescent lamps.

The source of collimated light may include one or more light sources of differing wavelengths.

The illuminating device may further comprise one or more detectors for detecting the reflected collimated light from the retina.

The source of collimated light may be located with the illuminating device, such that it rotates with the illuminating device.

The one or more detectors may be located with the illuminating device, such that they rotate with the illuminating device.

The source of collimated light may be located remotely from the illuminating device and the collimated light may be transmitted to the illuminating device by fibre optic, or the like.

The one or more detectors may be located remotely from the illuminating device and the reflected collimated light may be transmitted from the illuminating device by fibre optic, or the like.

The illuminating device may be capable of illuminating an area of the retina. That is, the illuminating device may be capable of illuminating a two-dimensional portion of the retina.

The scanning element may be a microelectromechanical systems (MEMS) scanning element. The MEMS scanning element may be a two-dimensional scanning element.

The illuminating device may be configured to illuminate the circumferential line on the retina by manipulating light from a source of light to produce a plurality of light beams which illuminate the retina of the eye. The plurality of light beams form a plane of light which illuminates the retina. The illuminating device may manipulate light from the source of light by passing the light through a line generating element such as a cylindrical lens, toroidal lens or gradient refractive index lens. That is, the illuminating device may be capable of manipulating light from the source of light by passing the light through a line generating element, or the like, to produce a plurality of light beams which illuminate the retina of the eye.

The illuminating device may be configured to illuminate the circumferential line on the retina by manipulating light from a source of collimated light to produce a plurality of collimated light beams which illuminate the retina of the eye. The plurality of collimated light beams form a plane of collimated light which illuminates the retina. The illuminating device may manipulate light from the source of collimated light by passing the light through a line generating element such as a cylindrical lens, toroidal lens or gradient refractive index lens. That is, the illuminating device may be capable of manipulating light from the source of collimated light by passing the collimated light through a line generating element, or the like, to produce a plurality of collimated light beams which illuminate the retina of the eye. In this arrangement light from the source of collimated light is manipulated such that the light is collimated in one dimension and divergent in another dimension.

The axis of rotation of the illuminating device may be parallel to a plane defined by the plurality of light beams produced by the illuminating device. That is, the plane of the axis of rotation of the illuminating device may be orthogonal to the plane of light beams produced by the illuminating device.

The axis of rotation of the illuminating device may lie on the plane defined by the plurality of light beams produced by the illuminating device.

The axis of rotation of the illuminating device may be parallel to a plane defined by the plurality of collimated light beams produced by the illuminating device. That is, the plane of the axis of rotation of the illuminating device may be orthogonal to the plane of collimated light beams produced by the illuminating device.

The illuminating device may comprise:
  a source of light; and
  a light manipulating element,
wherein the source of light and the light manipulating element combine to provide a plurality of light beams from a point; and
  the illuminating device further comprises a scan transfer device, wherein the scan transfer device has two foci and the point is provided at a first focus of the scan transfer device and the pupillary point of the eye is accommodated at a second focus of the scan transfer device, and wherein the scan transfer device transfers the plurality of light beams from the point into the eye.

The source of light may provide collimated light. That is, the illuminating device may comprise a source of collimated light.

The light manipulating element may be a collimated light manipulating element.

The light manipulating element may be a line generating element. The line generating element may be a cylindrical lens, toroidal lens or gradient refractive index lens.

The collimated light manipulating element may be a line generating element. The line generating element may be a cylindrical lens, toroidal lens or gradient refractive index lens.

The scan transfer device may comprise a tilted spherical mirror, an aspherical mirror, an elliptical mirror, an ellipsoidal mirror, a pair of parabola mirrors, a pair of paraboloidal mirrors or a lens system. In the case where the scan transfer device comprises a lens system, the lens system is arranged to provide two foci.

The front nodal point of the eye may be accommodated at the second focus of the scan transfer device.

The source of light may include a diverging laser diode and a toroidal lens or a lamp source with a slit aperture.

The source of collimated light may be a laser, a light emitting diode (LED), a Vertical Cavity Surface Emitting Laser (VCSEL), a super luminescent diode, a diode laser or a collimated incandescent lamp.

The source of collimated light may comprise one or more light sources. Alternatively, the source of collimated light may comprise one or more lasers, light emitting diodes (LEDs), Vertical Cavity Surface Emitting Lasers (VCSELs), super luminescent diodes, diode lasers or collimated incandescent lamps.

The source of light may include one or more light sources of differing wavelengths.

The source of collimated light may include one or more light sources of differing wavelengths.

The illuminating device may further comprise one or more detectors for detecting the reflected light from the retina.

The illuminating device may further comprise one or more detectors for detecting the reflected collimated light from the retina.

The source of light may be located with the illuminating device, such that it rotates with the illuminating device.

The source of collimated light may be located with the illuminating device, such that it rotates with the illuminating device.

The one or more detectors may be located with the illuminating device, such that they rotate with the illuminating device.

The source of light may be located remotely from the illuminating device and the light may be transmitted to the illuminating device by fibre optic, or the like.

The source of collimated light may be located remotely from the illuminating device and the collimated light may be transmitted to the illuminating device by fibre optic, or the like.

The illuminating device may be capable of illuminating an area of the retina. That is, the illuminating device may be capable of illuminating two-dimensional portion of the retina.

The illuminating device of the apparatus may be pivotable between a first position, in which the illuminating device may be used to illuminate a two-dimensional portion of the first retina of a first eye, and a second position, in which the illuminating device may be used to illuminate a two-dimensional portion of the second retina of a second eye.

The pivoting axis of the illuminating device may be orthogonal to the rotational axis of the illuminating device.

The apparatus may comprise two illuminating devices, wherein each illuminating device may be capable of illuminating a circumferential line on the retina and may be rotatable about an axis which lies substantially on the plane defined by the light source. The illuminating devices may be rotated together or separately. The illuminating devices may be located in a single housing, or located separately in two separate housings.

The illuminating devices are configured such that the circumferential lines on the retina illuminated by each device are in the same direction. That is, the circumferential lines illuminated by each device are parallel.

According to a second aspect of the present invention there is provided a system for illuminating the retina of each eye of a patient comprising two apparatuses according to the first aspect of the present invention, wherein each apparatus may be capable of illuminating the retina of one eye.

According to a third aspect of the present invention there is provided a method of illuminating the retina of an eye with collimated light comprising the steps of:
  providing an illuminating device including a planar light source capable of producing light in a plane, such that the illuminating device is capable of illuminating a circumferential line on the retina;
  providing a support structure,
  wherein the illuminating device is pivotably mountable to the support structure and is rotatable about an axis which lies substantially on the plane defined by the light source; and
  rotating the illuminating device about the axis to illuminate a plurality of circumferential lines on the retina with collimated light.

The axis of rotation of the illuminating device may lie on a horizontal plane defined by the optical axis of the eye. Alternatively, the axis of rotation of the illuminating device may be perpendicular to the horizontal plane defined by the optical axis of the eye. Alternatively, the axis of rotation of the illuminating device may not be parallel or perpendicular to the horizontal plane defined by the optical axis of the eye. In all of these arrangements, the axis of rotation of the illuminating device should lie on the plane defined by the light source.

The illuminating device may be configured such that its rotation about the axis is automated. The rotation of the imaging device may be computer-controlled.

According to a fourth aspect of the present invention there is provided an apparatus for imaging the retina of an eye comprising:
  an imaging device capable of obtaining a substantially one-dimensional image of the retina; and
  a support structure;
  wherein the imaging device is pivotably mounted to the support structure and is rotatable about an axis which is parallel to the direction of the substantially one-dimensional image, such that, in use, the imaging device may be rotated about the axis to obtain a plurality of substantially one-dimensional images of the retina, which may be combined to obtain a two-dimensional image of the retina.

The substantially one-dimensional image of the retina obtained by the imaging device is considered here to be an image having a length which is many times greater than its width. The direction of the substantially one-dimensional image is considered to be in the same direction as the length of the image.

The axis of rotation of the imaging device may be located around the pupillary point of the eye. The axis of rotation of the imaging device may be coincident with the front nodal point of the eye.

The axis of rotation of the imaging device may lie on a horizontal plane defined by the optical axis of the eye. Alternatively, the axis of rotation of the imaging device may be perpendicular to the horizontal plane defined by the optical axis of the eye. Alternatively, the axis of rotation of the imaging device may not be parallel or perpendicular to the horizontal plane defined by the optical axis of the eye. In all of these arrangements, the axis of rotation of the imaging device should remain parallel to the direction of the substantially one-dimensional image.

The imaging device may be configured such that its rotation about the axis is automated. The rotation of the imaging device may be computer-controlled.

The imaging device may be configured to obtain the substantially one-dimensional image of the retina by scanning collimated light across the retina of the eye. The imaging device may therefore be capable of performing a one-dimensional scan of collimated light across the retina of the eye.

The axis of rotation of the imaging device may be parallel to a plane defined by the substantially one-dimensional image collimated light scan produced by the imaging device. That is, the plane of the axis of rotation of the imaging device may be orthogonal to the plane defined by the one-dimensional collimated light scan it creates.

The axis of rotation of the imaging device may lie on the plane defined by the one-dimensional collimated light scan produced by the imaging device.

The imaging device may comprise:
  a source of collimated light; and
  a scanning element,
wherein the source of collimated light and the scanning element combine to provide a one-dimensional collimated light scan from a point; and
  the imaging device further comprises a scan transfer device, wherein the scan transfer device has two foci and the point is provided at a first focus of the scan transfer device and the pupillary point of the eye is accommodated at a second focus of the scan transfer device, and wherein the scan transfer device transfers the one-dimensional collimated light scan from the point into the eye.

The front nodal point of the eye may be accommodated at the second focus of the scan transfer device.

The scanning element may be an oscillating mechanism.

The scanning element may be an oscillating mirror, such as an oscillating plane mirror.

The scanning element may be a resonant scanner.

The scanning element may be a resonant mirror, such as a resonant scanning mirror.

The scanning element may be a microelectromechanical system (MEMS) scanning element. The MEMS scanning element may be a one-dimensional scanning element or a two-dimensional scanning element.

The scan transfer device may comprise a tilted spherical mirror, an aspherical mirror, an elliptical mirror, an ellipsoidal mirror, a pair of parabola mirrors, a pair of paraboloidal mirrors or a lens system. In the case where the scan transfer device comprises a lens system, the lens system is arranged to provide two foci.

The source of collimated light may be a laser, a light emitting diode (LED), a Vertical Cavity Surface Emitting Laser (VCSEL), a super luminescent diode, a diode laser or a collimated incandescent lamp.

The source of collimated light may include one or more light sources. The source of collimated light may include one or more lasers, light emitting diodes (LEDs), Vertical Cavity Surface Emitting Lasers (VCSELs), super luminescent diodes, diode lasers or collimated incandescent lamps.

The source of collimated light may include one or more light sources of differing wavelengths.

The imaging device may further comprise one or more detectors for detecting the reflected collimated light from the retina.

The source of collimated light may be located with the imaging device, such that it rotates with the imaging device.

The one or more detectors may be located with the imaging device, such that they rotate with the imaging device.

The source of collimated light may be located remotely from the imaging device and the collimated light may be transmitted to the imaging device by fibre optic, or the like.

The one or more detectors may be located remotely from the imaging device and the reflected collimated light may be transmitted from the imaging device by fibre optic, or the like.

The imaging device may be capable of obtaining a two-dimensional image of the retina. Therefore, in use, the imaging device may be rotated about the axis to obtain a plurality of two-dimensional images of the retina. The plurality of two-dimensional images may be combined to obtain a larger two-dimensional image of the retina. That is, the plurality of two-dimensional images may produce a montage two-dimensional image of the retina. In this arrangement, the plurality of two-dimensional images may be "stitched" to form a larger two-dimensional image of the retina. Alternatively, the plurality of two-dimensional images may be arranged to overlap in the direction of rotation of the imaging device. The plurality of overlapping two-dimensional images of the retina may be "stitched" to form the montage two-dimensional image of the retina.

The scanning element may be a microelectromechanical systems (MEMS) scanning element. The MEMS scanning element may be a two-dimensional scanning element.

The imaging device may be configured to obtain the substantially one-dimensional image of the retina by manipulating a source of light to produce a plurality of light beams which illuminate the retina of the eye. The plurality of light beams form a plane of light which illuminates the retina. The imaging device may manipulate the source of light by passing the light through a line generating element such as a cylindrical lens, toroidal lens or gradient refractive index lens. That is, the imaging device may be capable of manipulating the source of light by passing the light through a line generating element, or the like, to produce a plurality of light beams which illuminate the retina of the eye.

The imaging device may be configured to obtain the substantially one-dimensional image of the retina by manipulating a source of collimated light to produce a plurality of collimated light beams which illuminate the retina of the eye. The plurality of collimated light beams form a plane of collimated light which illuminates the retina. The imaging device may manipulate the source of collimated light by passing the light through a line generating element such as a cylindrical lens, toroidal lens or gradient refractive index lens. That is, the imaging device may be capable of manipulating the source of collimated light by passing the collimated light through a line generating element, or the like, to produce a plurality of collimated light beams which illuminate the retina of the eye. In this arrangement the source of collimated light is manipulated such that the light is collimated in one dimension and divergent in another dimension.

The axis of rotation of the imaging device may be parallel to a plane defined by the plurality of light beams produced by the imaging device. That is, the plane of the axis of rotation of the imaging device may be orthogonal to the plane of light beams produced by the imaging device.

The axis of rotation of the imaging device may be parallel to a plane defined by the plurality of collimated light beams produced by the imaging device. That is, the plane of the axis of rotation of the imaging device may be orthogonal to the plane of collimated light beams produced by the imaging device.

The axis of rotation of the imaging device may lie on the plane defined by the plurality of light beams produced by the imaging device.

The imaging device may comprise:
  a source of light; and
  a light manipulating element,
wherein the source of light and the light manipulating element combine to provide a plurality of light beams from a point; and
  the imaging device further comprises a scan transfer device, wherein the scan transfer device has two foci and the point is provided at a first focus of the scan transfer device and the pupillary point of the eye is accommodated at a second focus of the scan transfer device, and wherein the scan transfer device transfers the plurality of light beams from the point into the eye.

The source of light may provide collimated light. That is, the imaging device may comprise a source of collimated light.

The light manipulating element may be a collimated light manipulating element.

The light manipulating element may be a line generating element. The line generating element may be a cylindrical lens, toroidal lens or gradient refractive index lens.

The collimated light manipulating element may be a line generating element. The line generating element may be a cylindrical lens, toroidal lens or gradient refractive index lens.

The scan transfer device may comprise a tilted spherical mirror, an aspherical mirror, an elliptical mirror, an ellipsoidal mirror, a pair of parabola mirrors, a pair of paraboloidal mirrors or a lens system. In the case where the scan transfer device comprises a lens system, the lens system is arranged to provide two foci.

The front nodal point of the eye may be accommodated at the second focus of the scan transfer device.

The source of light may include a diverging laser diode and a toroidal lens or a lamp source with a slit aperture.

The source of collimated light may be a laser, a light emitting diode (LED), a Vertical Cavity Surface Emitting Laser (VCSEL), a super luminescent diode, a diode laser or a collimated incandescent lamp.

The source of collimated light may comprise one or more light sources. Alternatively, the source of collimated light may comprise one or more lasers, light emitting diodes (LEDs), Vertical Cavity Surface Emitting Lasers (VCSELs), super luminescent diodes, diode lasers or collimated incandescent lamps.

The source of light may include one or more light sources of differing wavelengths.

The source of collimated light may include one or more light sources of differing wavelengths.

The imaging device may further comprise one or more detectors for detecting the reflected light from the retina.

The imaging device may further comprise one or more detectors for detecting the reflected collimated light from the retina.

The source of light may be located with the imaging device, such that it rotates with the imaging device.

The source of collimated light may be located with the imaging device, such that it rotates with the imaging device.

The one or more detectors may be located with the imaging device, such that they rotate with the imaging device.

The source of light may be located remotely from the imaging device and the light may be transmitted to the imaging device by fibre optic, or the like.

The source of collimated light may be located remotely from the imaging device and the collimated light may be transmitted to the imaging device by fibre optic, or the like.

The imaging device may be capable of obtaining a two-dimensional image of the retina. Therefore, in use, the imaging device may be rotated about the axis to obtain a plurality of two-dimensional images of the retina. The plurality of two-dimensional images may be combined to obtain a larger two-dimensional image of the retina. That is, the plurality of two-dimensional images may produce a montage two-dimensional image of the retina. In this arrangement, the plurality of two-dimensional images may be "stitched" to form a larger two-dimensional image of the retina. Alternatively, the plurality of two-dimensional images may be arranged to overlap in the direction of rotation of the imaging device. The plurality of overlapping two-dimensional images of the retina may be "stitched" to form the montage two-dimensional image of the retina.

The imaging device of the apparatus may be pivotable between a first position, in which the imaging device may be used to obtain a two-dimensional image of the first retina of a first eye, and a second position, in which the imaging device may be used to obtain a two-dimensional image of the second retina of a second eye.

The pivoting axis of the imaging device may be orthogonal to the rotational axis of the imaging device.

The apparatus may comprise two imaging devices, wherein each imaging device may be capable of obtaining a substantially one-dimensional image of the retina and may be rotatable about an axis which is parallel to the direction of the substantially one-dimensional image. The imaging devices may be rotated together or separately. The imaging devices may be located in a single housing, or located separately in two separate housings.

The imaging devices are configured such that the substantially one-dimensional images obtained by each device are in the same direction. That is, the substantially one-dimensional images obtained by each device are parallel.

The apparatus may further comprise one or more data processing devices for storing the plurality of at least one-dimensional images and/or combining the images to obtain the two-dimensional image.

According to a fifth aspect of the present invention there is provided a method of imaging the retina of an eye comprising the steps of:

providing an imaging device capable of obtaining a substantially one-dimensional image of the retina, wherein the imaging device is rotatable about an axis which is parallel to the direction of the substantially one-dimensional image;

providing a support structure;

wherein the imaging device is pivotably mountable to the support structure;

rotating the imaging device about the axis to obtain a plurality of substantially one-dimensional images of the retina; and combining the plurality of substantially one-dimensional images to obtain a two-dimensional image of the retina.

The axis of rotation of the imaging device may lie on a horizontal plane defined by the optical axis of the eye. Alternatively, the axis of rotation of the imaging device may be perpendicular to the horizontal plane defined by the optical axis of the eye. Alternatively, the axis of rotation of the imaging device may not be parallel or perpendicular to the horizontal plane defined by the optical axis of the eye. In all of these arrangements, the axis of rotation of the imaging device should remain parallel to the direction of the substantially one-dimensional image.

The imaging device may be configured such that its rotation about the axis is automated. The rotation of the imaging device may be computer-controlled.

According to a sixth aspect of the present invention there is provided an apparatus for treating the retina of an eye with collimated light comprising:

an illuminating device including a planar light source capable of producing light in a plane, such that the illuminating device is capable of illuminating a circumferential line on the retina; and a support structure;

wherein the illuminating device is pivotably mountable to the support structure and is rotatable about an axis which lies substantially on the plane defined by the light source, such that, in use, the illuminating device may be rotated about the axis to illuminate a plurality of circumferential lines on the retina with collimated light.

Treatment of the retina is interpreted here to include photodynamic therapy, photo-ablation, photoporation, photoactivation or other methods where the interaction of the light is used to alter the state or structure of the retina or to alter the state of chemicals within the retinal structure.

According to a seventh aspect of the present invention there is provided a method of treating the retina of an eye with collimated light comprising the steps of:

providing an illuminating device including a planar light source capable of producing light in a plane, such that the illuminating device is capable of illuminating a circumferential line on the retina;

providing a support structure, wherein the illuminating device is pivotably mountable to the support structure and is rotatable about an axis which lies substantially on the plane defined by the light source; and rotating the illuminating device about the axis to illuminate a plurality of circumferential lines on the retina with collimated light.

Embodiments of the present invention will now be described, by way of example only, with reference to the accompanying drawings, in which:—

FIG. 5 is a schematic illustration of the unfolded light beam path of FIG. 3;

FIG. 6 is a more detailed illustration of FIG. 5;

Figure 9:
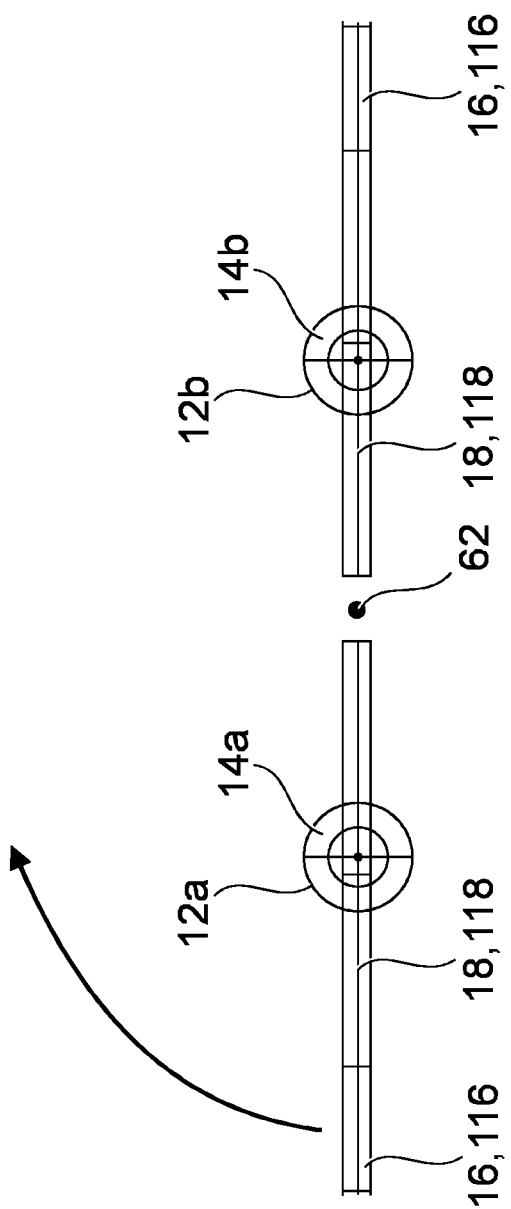

FIG. 9 a schematic illustration of the operation of the apparatus of the present invention when imaging two eyes.

Figure 1:
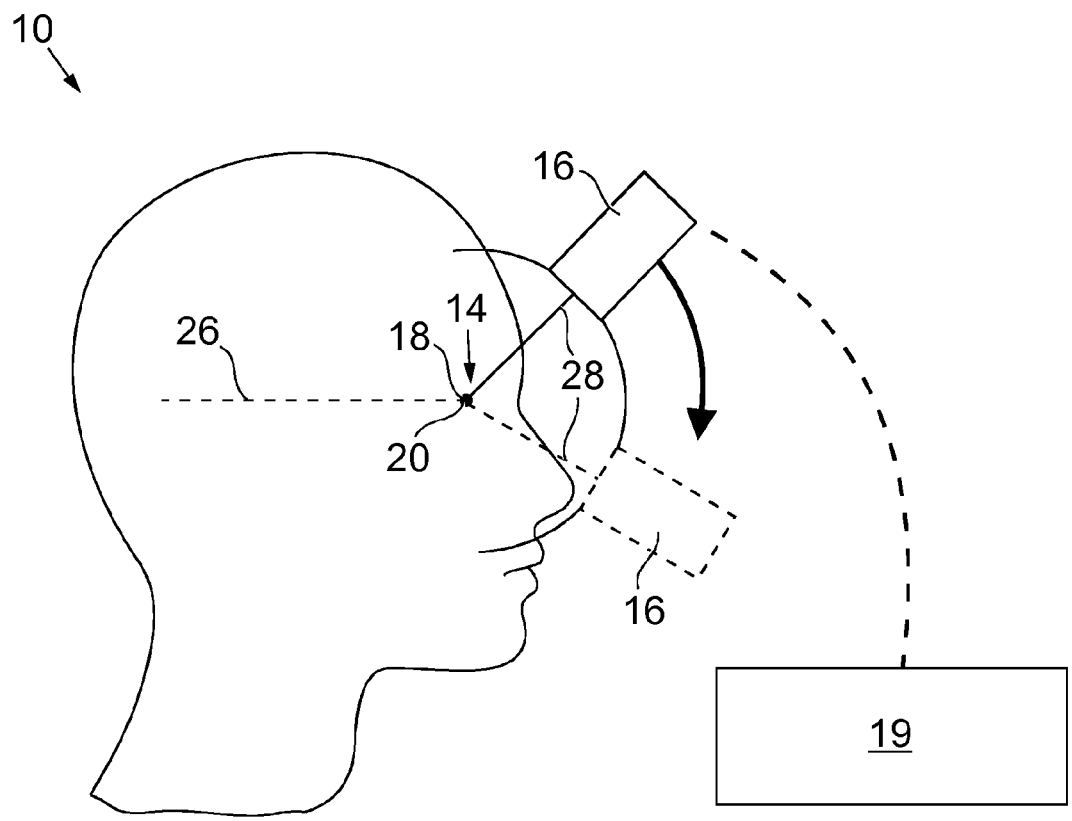
FIG. 1 is schematic side view of an apparatus for illuminating, imaging and treating the retina of an eye according to the present invention.
Figure 2:
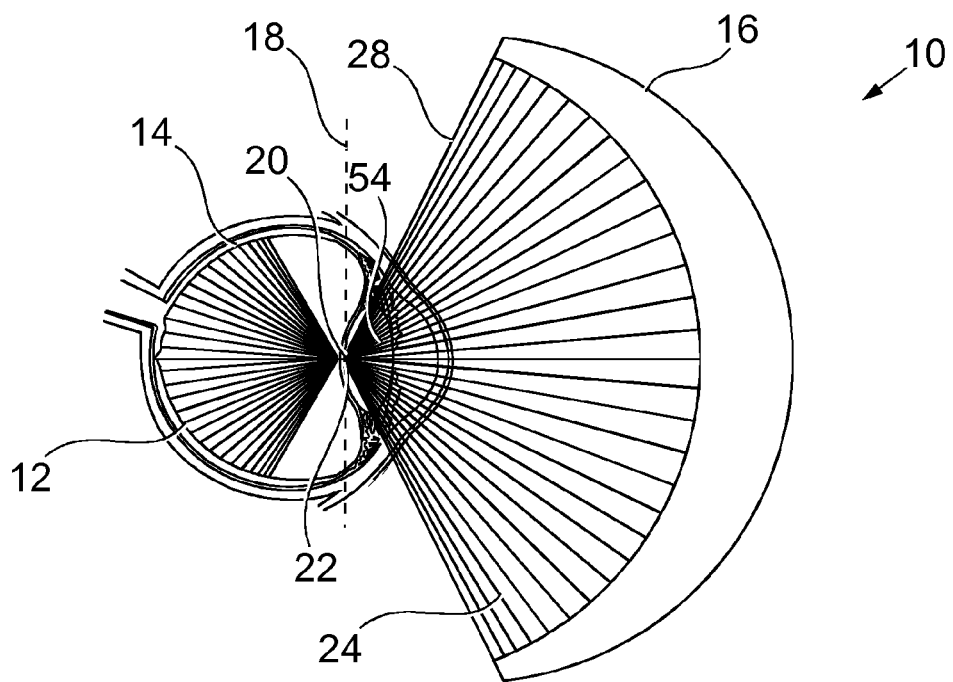
FIG. 2 is a schematic top view of the apparatus of FIG. 1 which details the light rays entering the eye.

FIGS. 1 and 2 illustrate an apparatus 10 for illuminating, imaging and treating the retina 12 of an eye 14. The apparatus 10 includes an imaging device 16 which is capable of obtaining a substantially one-dimensional image of the retina 12. That is, the imaging device 16 is capable of obtaining a line image of the retina 12.

The apparatus 10 also includes a support structure (not shown) for supporting the imaging device 16. The imaging device 16 is pivotably mounted to the support structure. The support structure may include a base member which may be mounted to a desk, or the like. Alternatively, the support structure may include headgear, which may, for example, be worn by a patient.

In the embodiment described here the apparatus 10 includes an imaging device 16 which is capable of obtaining a substantially one-dimensional image of the retina 12. However, it should be appreciated that the apparatus 10 may alternatively include an illuminating device, which, instead of obtaining an image of the retina, simply illuminates the retina with collimated light. The illuminating device may include a planar light source and is capable of producing light in a plane, such that the illuminating device is capable of illuminating a circumferential line on the retina.

As illustrated in FIG. 1, the imaging device 16 is rotatable about the eye 14. As illustrated in FIG. 2, the imaging device 16 is rotatable about an axis 18. The axis 18 is located in the region of the pupillary point 20 of the eye 14. The axis 18 may be coincident with the front nodal point 22 of the eye 14. The axis 18 is parallel to the direction of the substantially one-dimensional image of the retina 12 (see FIG. 2). The axis 18 lies on a plane of light 24 produced by the imaging device 16. FIG. 2 illustrates the rays of light 28 generated by the imaging device 16 to image the retina 12. It should be noted that the refraction of the light rays 28 by the lens of the eye 14 have been omitted for clarity.

As the imaging device 16 is rotated about the axis 18, a plurality of one-dimensional images of the retina 12 are obtained. These images are then combined to form a two-dimensional image of the retina 12. The apparatus 10 includes one or more data processing devices (not shown) which are used to store the plurality of one-dimensional images and/or combine them to form the two-dimensional image.

The imaging device 16 is rotated through the axis 18 at a fast enough rate to avoid large eye motion. Typically, a full rotation takes around 100 ms to 200 ms. However, it should be appreciated that slower or faster scanning rates may be used.

Figure 3:
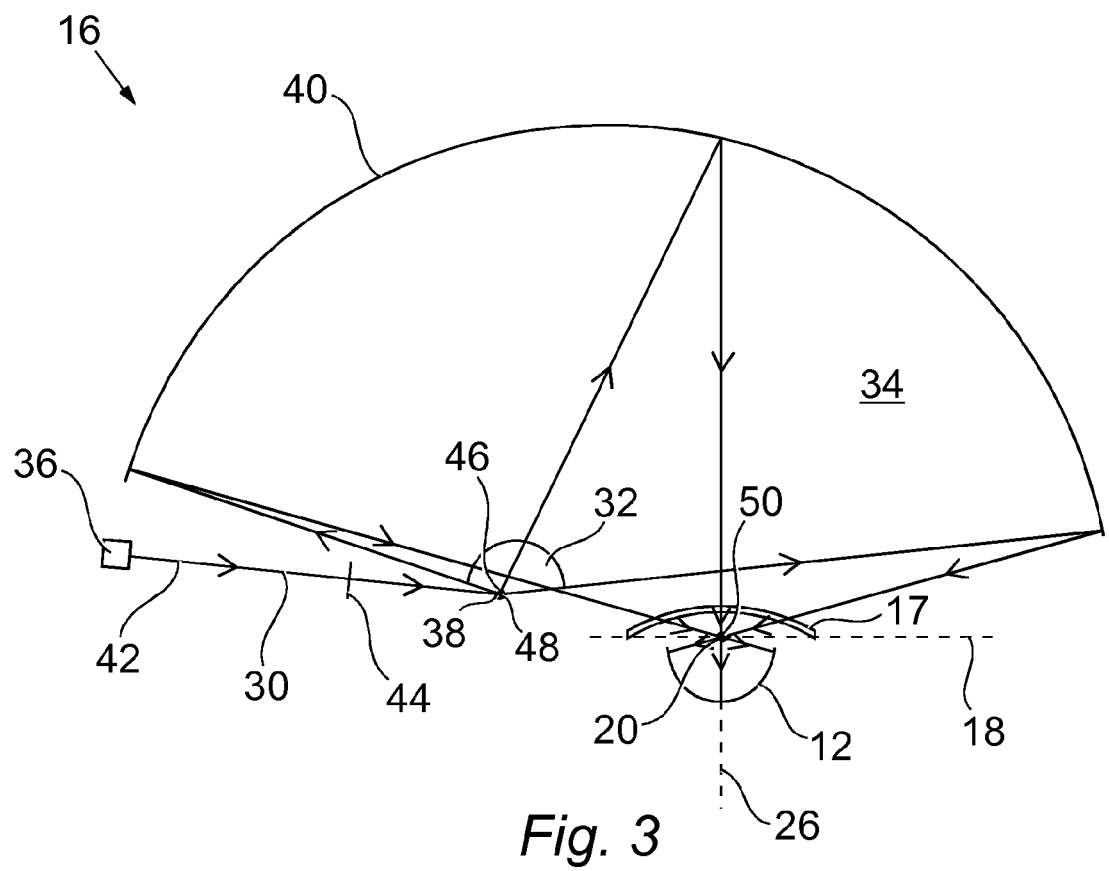
FIG. 3 is a schematic top view of a first embodiment of the imaging device of the imaging apparatus of FIG. 1.
Figure 4:
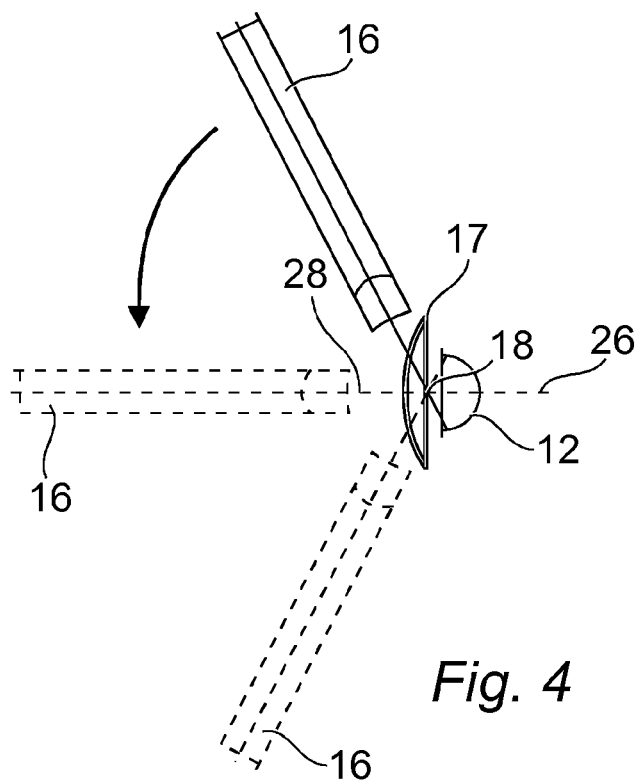
FIG. 4 is a side view of FIG. 3.

FIGS. 3 and 4 are schematic illustrations of a first embodiment of the imaging device 16. The imaging device 16 in this embodiment is configured to obtain a one-dimensional image of the retina 12 by scanning collimated light 30 across the retina 12 of the eye 14. That is, the imaging device 16 is therefore capable of performing a one-dimensional scan 32 of collimated light 30 across the retina 12 of the eye 14.

In this embodiment, the rotational axis 18 of the imaging device 16 is parallel to a plane 34 produced by the one-dimensional collimated light scan 32 produced by the imaging device 16. That is, the rotational axis 18 of the imaging device 16 lies on the plane 34 defined by the one-dimensional collimated light scan 32 produced by the imaging device 16, and the plane of the rotational axis 18 of the imaging device 16 is orthogonal to the plane 34 defined by the one-dimensional collimated light scan 32 produced by the imaging device 16.

With reference to FIG. 3 in particular, the imaging device 16 comprises a source of collimated light 36, a scanning element 38 and a scan transfer device 40.

The source of collimated light 36 transmits light 30 to the scanning element 38 via a focussing lens 44 (see below). The focussing lens 44 provides collimated light to the eye 14 via the scan transfer device 40 (see below). In the embodiment described here, the scanning element 38 is a one-dimensional microelectromechanical system (MEMS) scanner. However, it should be appreciated that alternative scanning elements could also be used. The scanning element 38 scans the collimated light 30 across the scan transfer device 40. The source of collimated light 36 and the scanning element 38 combine to produce the one-dimensional collimated light scan 32 from a point 46.

The scan transfer device 40, which, in the embodiment described and illustrated here is an ellipsoidal mirror, has two foci; a first focal point 48 and a second focal point 50. The point 46, from which the one-dimensional collimated light scan 32 emanates, is located at the first focal point 48 of the scan transfer device 40 and the pupillary point 20 of the eye 14 is located at the second focal point 50 of the scan transfer device 40. Since the scan transfer device 40 has two focal points 48, 50, the scan transfer device 40 transfers the one-dimensional collimated light scan 32 from the point 46 into the eye 14. Thus, the imaging device 16 obtains a one-dimensional image of the retina 12 by scanning the collimated light 30 across the retina 12 of the eye 14.

The distance between the two foci 48, 50 of the scan transfer device 40 is approximately 40 mm to 150 mm. It is preferable that the distance between the two foci 48, 50 of the scan transfer device 40 is 50 mm to 60 mm. This arrangement reduces the degree of variable magnification and focal offset during scanning.

The rotational axis 18 of the imaging device 16 also lies on the second focal point 50 of the scan transfer device 40. That is, in the embodiment illustrated and described here, the rotational axis 18 of the imaging device 16 is located at the pupillary point 20 of the eye 14 and the second focal point 50 of the scan transfer device 40.

As described above, and with reference to FIG. 4, as the imaging device 16 is rotated about the axis 18 a plurality of one-dimensional images of the retina 12 are obtained. These images are then combined to form a two-dimensional image of the retina 12.

The source of collimated light 36 in the embodiment described and illustrated here is a laser. The laser 36 is coupled into a first optical fibre 42, which is a single mode polarisation maintaining fibre. The laser 36 may be located in a housing 19 (see FIG. 1) which is remote from the imaging device 16 and the first optical fibre 42 transfers the collimated light 30 from the laser 36 to the imaging device 16. In this arrangement the imaging device 16 is moveable with respect to the housing 19. Alternatively, the laser 36 may be located with the imaging device 16 and the laser 36 and first optical fibre 42 rotate with the imaging device 16.

The imaging device 16 also includes a protective window 17, which protects the eye 14 from dust and debris. The protective window 17 may be mounted around the eye 14 so that its position is fixed relative to the eye 14, or the protective window 17 may be mounted with the imaging device 16 so that it rotates with the imaging device 16.

With reference to FIG. 5, the diverging light emitted by the first optical fibre 42 is refocused to the retina 12 of the eye 14 through the combination of a focussing lens 44, the scan transfer device 40 and the lens 54 of the eye 14. As illustrated in FIG. 5, the retinal planes are labelled (R) and the pupil planes are labelled (P).

With reference to FIG. 6, reflected light from the retina 12 is refocused to a second optical fibre 56 through the combination the lens 54 of the eye 14, the scan transfer device 40 and the focussing lens 44. The second optical fibre 56 is a multi-mode optical fibre with a large diameter core.

As illustrated in FIG. 6, a beam splitter 58 is positioned between the first and second optical fibres 42, 56. The beam splitter 58 is a plate glass beam splitter and is oriented at 45 degrees to the focussing lens 44. The beam splitter 58 reflects a portion of the collimated light 30 emitted from the first optical fibre 42 to the focussing lens 44 and into the eye 14. The beam splitter 58 may be uncoated and provides approximately 90/10 splitting ratio by utilising polarisation specific Fresnel reflections. The use of single mode polarisation maintaining optical fibres allows a stable optical power to be achieved during scanning. Approximately 90% of the light from the first optical fibre 42 is transmitted through the beam splitter 58, with the remaining 10% going to the eye 14. The light transmitted through the beam splitter 58 on input may be used to monitor the power of the collimated light 30 for safety reasons.

The majority of the reflected light from the retina 12 is transmitted through the beam splitter 58 and focussed to the second optical fibre 56. The second optical fibre 56 is connected to at least one fast single point photo-detector element 60, such as an avalanche photo detector APD photo-detector, PIN diode, photomultiplier tube (PMT), silicon photo multiplier (SPM), or similar single point detectors. The detector 60 may be located in the housing 19 which is remote from the imaging device 16 and the second optical fibre 56 transfers the reflected collimated light 30 from the imaging device 16 to the detector 60. In this arrangement the imaging device 16 is moveable with respect to the housing 19. Alternatively, the detector 60 may be located with the imaging device 16 and the detector 60 and second optical fibre 56 rotate with the imaging device 16.

The apparatus 10 also includes at least one data processing device (not shown), such as a computer, for storing the plurality of at least one-dimensional images and combining the images to obtain the two-dimensional image. The data processing device is located remotely from the imaging device 16 and may be located within the housing 19.

If the laser 36 and detector 60 are located with the imaging device 16, the apparatus 10 may further comprise one or more data communication devices, such as optical fibres etc., to allow the data processing device to communicate with, and/or control, the laser 36 and detector 60. The communication between the imaging device 16 and the data processing device may be wireless.

The apparatus 10 may also be capable of performing multiple wavelength imaging. Multiple wavelength imaging may be achieved, for example, by providing multiple lasers combined into one optical fibre, which is time-multiplexed and synchronised with a single detector.

Alternatively, two single mode optical fibres could transmit the collimated light from two different sources of collimated light into the beam path. In this arrangement, the lasers would again be time-multiplexed with a single detector. In order to avoid time-multiplexing, a further beam splitter with wavelength splitting properties may be inserted between the beam splitter 58 and the second optical fibre 56, such that the second optical fibre 56 transmits light of different wavelength bands to two single point photo detectors.

Figure 7:
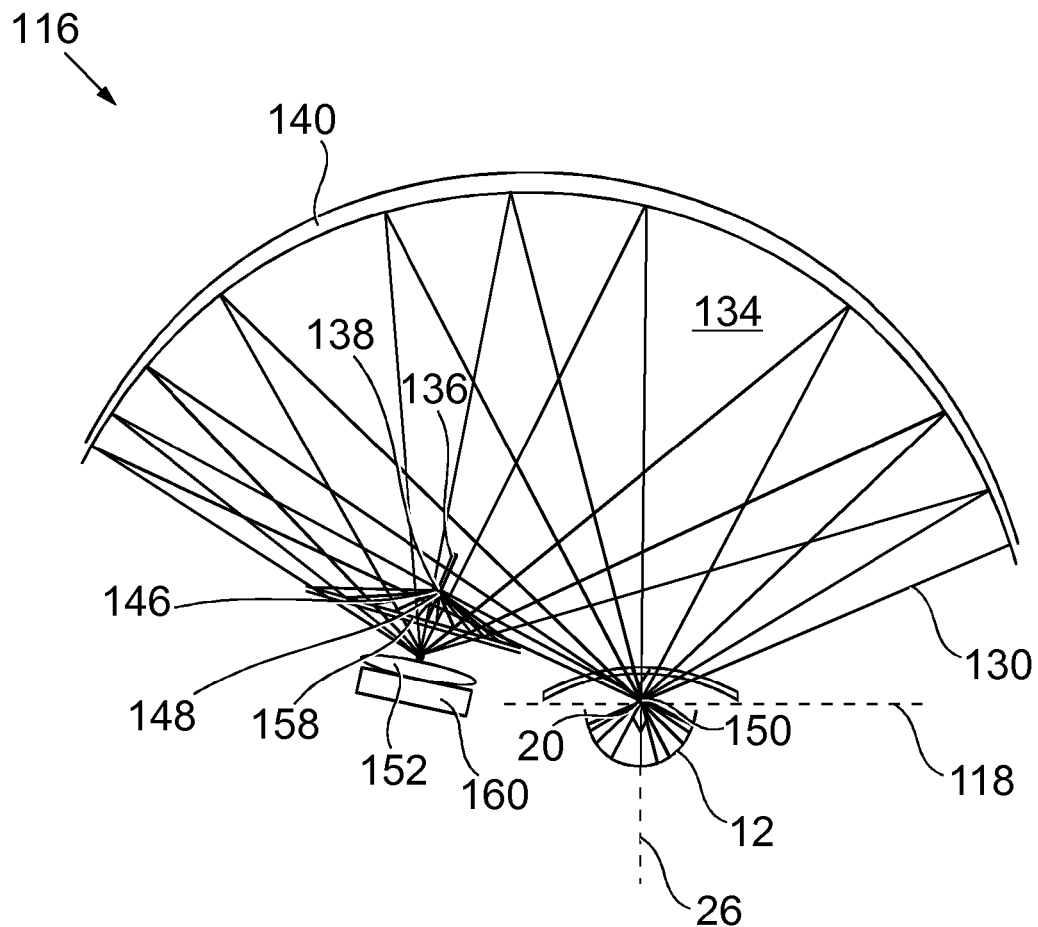
FIG. 7 is a schematic top view of a second embodiment of the imaging device of the imaging apparatus of FIG. 1.
Figure 8:
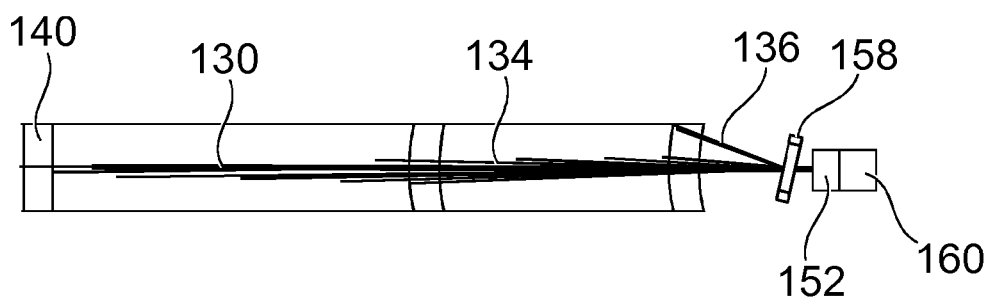
FIG. 8 is a side view of FIG. 7.

FIGS. 7 and 8 are schematic illustrations of a second embodiment of the imaging device 116 of the apparatus 10. The imaging device 116 in this embodiment is configured to obtain a substantially one-dimensional image of the retina 12 by manipulating light from a source of light 136 to produce a plurality of light beams 130 which illuminate the retina 12 of the eye 14. The plurality of light beams 130 form a plane of light 134 which illuminates the retina 12. The imaging device 116 may manipulate light from the source of light 136 by passing the light through a line generating element 138, such as a cylindrical lens, toroidal lens or gradient refractive index lens. That is, the imaging device 116 is therefore capable of manipulating the source of light 136 by passing the light through a line generating element, or the like, to produce a plurality of light beams 130 which illuminate the retina 12 of the eye 14.

The source of light 136 may include, a diverging laser diode and a toroidal lens, a lamp source with a slit aperture, a light emitting diode (LED), a Vertical Cavity Surface Emitting Laser (VCSEL), a super luminescent diode, a diode laser or a collimated incandescent lamp.

The light beam produced by the source of light 136 may be collimated. That is, the apparatus may use a collimated light source to illuminate the retina 12 of the eye 14.

In this embodiment, the rotational axis 118 of the imaging device 116 is parallel to the plane 134 produced by the imaging device 116. That is, the rotational axis 118 of the imaging device 116 lies on the plane 134 defined by the plurality of light beams 130 produced by the imaging device 116, and the plane of the rotational axis 118 of the imaging device 116 is orthogonal to the plane 134 defined by the plurality of light beams 130 produced by the imaging device 116.

With reference to FIGS. 7 and 8, the arrangement of the second embodiment of the imaging device 116 is similar to the arrangement of the first embodiment (FIGS. 3 and 4). The imaging device 116 comprises a source of light 136, a light manipulating element 138 and a scan transfer device 140.

In the embodiment described here the source of light 136 is a laser.

However, it should be appreciated that the source of light does not necessarily have to be collimated.

The source of collimated light 136 transmits collimated light 130 to the light manipulating element 138. The source of collimated light 136 and the light manipulating element 138 combine to produce a plurality of light beams 130 from a point 146.

The scan transfer device 140 is identical to that described in relation to the first embodiment of the imaging device 16. The point 146 from which the plurality of light beams 130 emanate is located at the first focal point 148 of the scan transfer device 140 and the pupillary point 20 of the eye 14 is located at the second focal point 150 of the scan transfer device 140. Again, since the scan transfer device 140 has two focal points 148, 150, the scan transfer device 140 transfers the plurality of light beams 130 from the point 146 into the eye 14. Thus, the imaging device 116 obtains a one-dimensional image of the retina 12 by illuminating the retina 12 of the eye 14 with a plane of light 134 and detecting the reflected light therefrom.

The rotational axis 118 of the imaging device 116 again lies on the second focal point 150 of the scan transfer device 140. That is, in the embodiment illustrated and described here, the rotational axis 118 of the imaging device 116 is located at the pupillary point 20 of the eye 14 and the second focal point 150 of the scan transfer device 140.

The apparatus 100 also includes a support structure (not shown) for supporting the imaging device 116. The imaging device 116 is pivotably mounted to the support structure. The support structure may include a base member which may be mounted to a desk, or the like. Alternatively, the support structure may include headgear, which may, for example, be worn by a patient.

Again as described above, as the imaging device 116 is rotated about the axis 118 a plurality of one-dimensional images of the retina 12 are obtained. These images are then combined to form a two-dimensional image of the retina 12.

The laser 136 is coupled into the first optical fibre, which is a single mode polarisation maintaining fibre. The laser 136 may be located in the housing 19 which is remote from the imaging device 116 and the first optical fibre transfers the collimated light 130 from the laser 136 to the imaging device 116. In this arrangement the imaging device 116 is again moveable with respect to the housing 19. Alternatively, the laser 136 may be located with the imaging device 116 and the laser 136 and first optical fibre rotate with the imaging device 116.

With reference to FIG. 7, the collimated light 130 illuminates the retina 12 of the eye 14 through the combination of the light manipulating element 138, the scan transfer device 140 and lens of the eye 14.

A beam splitter 158 is positioned between the light manipulating element 138 and the scan transfer device 140. Reflected light from the retina 12 is refocused to a detector 160 through the combination of the lens 54 of the eye 14, the scan transfer device 140 and a focussing lens 152. The detector 160 is a linear array of photo detection elements, such as a CCD or CMOS device. The detector 160 in this embodiment should be a line array. However, it should be appreciated that the line array could be one-dimensional or two-dimensional.

The beam splitter 158 is a plate glass beam splitter and is oriented at 45 degrees to the focussing lens 152. It should be appreciated that the beam splitter 158 does not necessarily need to be oriented at 45 degrees and other angles of orientation are possible with the same effect. Approximately 90% of the light from the scan transfer device 140 is transmitted through the beam splitter 158 and focussed by the focussing lens 152 to the detector 160.

The detector 160 may be located in the housing 19 which is remote from the imaging device 116 and a second optical fibre (not shown) may transfer the reflected collimated light 130 from the imaging device 116 to the detector 160. In this arrangement the imaging device 116 is moveable with respect to the housing 19. Alternatively, the detector 160 may be located with the imaging device 116 and the detector 160 rotates with the imaging device 116.

If the laser 136 and detector 160 are located with the imaging device 116, the apparatus 10 may further comprise one or more data communication devices, such as optical fibres etc., to allow the data processing device to communicate with, and/or control, the laser 136 and detector 160.

The imaging device 116 also includes a protective window 117, which protects the eye 14 from dust and debris. The protective window 117 may be mounted around the eye 14 so that its position is fixed relative to the eye 14, or the protective window 117 may be mounted with the imaging device 16 so that it rotates with the imaging device 116.

Multiple wavelength imaging may again be achieved by providing multiple lasers with different wavelengths. Again, a beam splitter with wavelength splitting properties may be inserted between the scan transfer device 140 and the one or more detectors 160. In this arrangement detector 160 may be provided with a Bayer filter to facilitate multiple wavelength detection.

With reference to FIG. 9, the imaging device 16, 116 may be pivotable about an axis 62. The axis 62 is orthogonal to the rotational axis 18, 118 of the imaging device 16, 116. The imaging device is therefore pivotable between a first position (left side of FIG. 9), in which the imaging device 16, 116 may be used to obtain a two-dimensional image of the first retina 12a of a first eye 14a, and a second position (right side of FIG. 9), in which the imaging device 16, 116 may be used to obtain a two-dimensional image of the first retina 12b of a second eye 14b. The apparatus 10 can therefore image both eyes of a patient.

The imaging device 16, 116 may be configured such that is rotation about the axis 18, 118 may be controlled by a computer, or the like. This allows the imaging process to be automated, which increases the speed in which the two-dimensional image is created. This also improves the repeatability of the image acquisition.

The imaging device may be configured such that its rotation about the axis is automated. The rotation of the imaging device may be computer-controlled.

The apparatus 10 of the present invention can be manufactured at a lower cost than known retinal imaging apparatus, such as scanning laser ophthalmoscopes (SLOs), as the apparatus 10 does not require conventional laser scanning elements, such as polygon mirrors. The apparatus 10 can be made more compact than known retinal imaging apparatuses, since the apparatus uses a smaller number of components than known retinal imaging apparatuses. The apparatus 10 of the present invention also includes a smaller number of optical surfaces, which increases the optical efficiency of the apparatus. The result of this is that, for the same amount of input power to the eye, the total power at the imaging detector is higher than known methods. Also, because the rotation of the entire imaging device 16, 116 is about the pupillary point of the eye, only a single, small sized, scan transfer device is required. This reduces the cost and size of the apparatus. Also, the apparatus 10 may be capable of performing "wide field" imaging or "narrow field" imaging. Therefore, the apparatus is scalable for different markets. Furthermore, depending on the geometry of the scan transfer device, no focal correction is necessary to achieve high resolution imaging. This yields higher resolution images than known methods. Also, the apparatus 10 supports loose confocal imaging to avoid back reflections from a window, cornea and other surfaces. This means that for point scans or line scans an aperture can be used to block reflections from the cornea that would otherwise cause lack of contrast and artefacts in the image.

Modifications and improvements may be made to the above without departing from the scope of the present invention. For example, although the rotational axis 18 of the imaging device 16 has been illustrated and described above as being coincident with the pupillary point 20 of the eye 14, it should be appreciated that the axis 18 could be located generally around the front nodal point 22 of the eye 14. That is, the axis 18 could be located on the optical axis 26 in front of the lens, in the plane of the iris, or at the rear nodal point of the eye 14. In order to achieve the widest field of view, i.e. to avoid clipping of the light beam, the axis 18 should be located at the front of the lens of the eye 14, i.e. in the plane of the iris. The rotational axis 18 of the imaging device 16 is therefore within +/−4 mm of the plane of the iris.

Furthermore, although the rotational axis 18 of the imaging device 16 has been illustrated and described above as lying on the horizontal plane 24 defined by the optical axis 26 of the eye 14, it should be appreciated that the rotational axis 18 of the imaging device 16 may be perpendicular to the horizontal plane 24. Alternatively, the rotational axis 18 of the imaging device 16 may be neither parallel nor perpendicular to the horizontal plane 24. In any of these arrangements the axis of rotation 18 of the imaging device 16 should remain parallel to the direction of the one-dimensional image.

Also, although the pupillary point 20 of the eye 14 has been described above as being located at the second focal point 50 of the scan transfer device 40, it should be appreciated that the pupillary point 20 of the eye 14 includes any point in the region of the pupillary point 20 on the optical axis 26 in front of the lens, in the plane of the iris, the front nodal point of the eye 14, or the rear nodal point of the eye 14. Therefore, any point in the region of the pupillary point 20, which includes the region in front of the lens, in the plane of the iris, the front nodal point of the eye 14, or the rear nodal point of the eye 14, could be located at the second focal point 50 of the scan transfer device 40.

Furthermore, although the source of collimated light 36 has been described above as a laser, it should be appreciated that the source of collimated light 36 may alternatively be a light emitting diode (LED), a Vertical Cavity Surface Emitting Laser (VCSEL), a super luminescent diode, a diode laser or a collimated incandescent lamp.

Also, although the beam splitter 58 has been described above as providing 90/10 splitting ratio, it should be appreciated that beam splitters with other splitting ratios may be used, such as 80/20, 50/50, or other types of beam splitters, such as aperture beam splitters, polarisation beam splitters, dichroic mirrors (for fluorescence imaging) where the input beam diameter is smaller than the output beam diameter. Also, the beam splitter 158 may again be oriented at other suitable angles than 45 degrees with the same effect.

Furthermore, although the scanning element has been illustrated and described above as being a MEMS scanner, it should be appreciated that the scanning element could be any oscillating mechanism suitable for scanning the collimated light 30 across the scan transfer device 40. This may include resonant scanners, oscillating plane mirrors and the like. The scanning element should preferably be capable of operating at high speed (i.e. above 5 kHz) and provide a high amplitude of scan (i.e. up to 180 degrees).

Also, although the scan transfer device 40 has been illustrated and described above as an ellipsoidal mirror, it should be appreciated that the scan transfer device 40 may alternatively be a tilted spherical mirror, an aspherical mirror, an elliptical mirror, an ellipsoidal mirror, a pair of parabola mirrors, a pair of paraboloidal mirrors or a lens system.

Furthermore, although the imaging device 16, 116 has been described above as being capable of obtaining a one-dimensional image of the retina 12, i.e. a line image of the retina 12, and that a two-dimensional image of the retina is obtained by combining a number of these images together, it should be appreciated that the imaging device may be capable of obtaining a two-dimensional image of the retina. Therefore, in use, the imaging device may be rotated about the axis to obtain a plurality of two-dimensional images of the retina. The plurality of two-dimensional images may be combined to obtain a larger two-dimensional image of the retina.

That is, the plurality of two-dimensional images may produce a montage two-dimensional image of the retina. In this arrangement, the plurality of two-dimensional images may be "stitched" to form a larger two-dimensional image of the retina. Alternatively, the plurality of two-dimensional images may be arranged to overlap in the direction of rotation of the imaging device. The plurality of overlapping two-dimensional images of the retina may be "stitched" to form the montage two-dimensional image of the retina. In this arrangement a two-dimensional scanning element may be used to obtain the plurality of two-dimensional images of the retina. The scanning element is capable of scanning in two directions. At least one of the scan directions should be in the same direction as the axis of rotation of the imaging device. The two-dimensional images may have a rectangular aspect ratio, such as 1000:100. However, it should be appreciated that the aspect ratio could be any desired value. The two-dimensional images are acquired at a fast frame rate, such as 30 frames per second, to avoid eye motion. The imaging device in this arrangement may be rotated at a slower rate than the arrangement described above. The two-dimensional images are then combined to form a larger two-dimensional image, such as an image with an aspect ratio of 1000:800 or 1000:1000. The scanning element may be a two-dimensional MEMS scanner. In this arrangement, the two-dimensional images may be captured using a two-dimensional rectangular array, as described above.

Also, although the apparatus 10 has been illustrated and described above as comprising a single imaging device 16, 116, it should be appreciated that the apparatus 10 may comprise two imaging devices 16. 116, wherein each imaging device 16, 116 may be capable of obtaining at least a one-dimensional image of the retina and may be rotatable about an axis which is parallel to the direction of the at least one-dimensional image. In this arrangement the imaging devices 16, 116 may be rotated together or separately. The imaging devices 16, 116 may be located in a single housing, or located separately in two separate housings. This arrangement allows two eyes to be imaged at the same time.

Furthermore, it should be appreciated that the apparatus 10, 100 may also be used for fluorescence imaging by imaging at one wavelength and detecting at another, as is common in applications such as angiography and auotofluorescence imaging. It should therefore be appreciated that the apparatus 10, 100 may obtain an image of the retina by receiving light reflected from the retina or fluorescent light emitted by the retina on excitation thereof.

Also, although the apparatus 10, 100 has been described above as for illuminating and imaging the retina 12 of the eye 14, it should be appreciated that the apparatus 10, 100 may also be used to administer treatment to the retina 12 by illuminating the retina 12 with collimated light of a suitable wavelength and/or power. Treating the retina 12 may include the following steps: (i) identifying a region of the retina for treatment, (ii) specifying the size of the treatment area through treatment planning, linked to an imaging system and (iii) guiding the treatment either through manual control or pre-specified automated control to deliver the treatment illumination to single or multiple sites via a common input path to the imaging source(s). This provides a correlation between the treatment geography and treatment planning derived from the imaging system. Treating the retina 12 may also include the optional steps of viewing an image of the retina 12 during the treatment and/or re-imaging the retina to confirm the treatment is successful.

That is, the present invention also provides an apparatus for illuminating the retina with collimated light for use in treating the retina. The present invention also provides a method for illuminating the retina with collimated light for use in treating the retina.

The invention claimed is:

1. An apparatus for illuminating the retina of an eye comprising:
   an illuminating device including a light source capable of producing light in a plane, the light radiating in said plane from a first point such that the illuminating device illuminates a circumferential line on the retina lying on said plane and centered on a second point; and
   a support structure;
   wherein the illuminating device is pivotably mountable to the support structure and is automatically rotatable about an axis which lies substantially on the plane defined by the light source and which extends through said second point, such that the illuminating device automatically rotates about the axis to illuminate an area of the retina by scanning the circumferential line illuminated by the light about said axis, and
   wherein the illuminating device further comprises a scan transfer device, wherein the scan transfer device has first and second foci, the first point is provided at the first focus of the scan transfer device, the second point is provided at the second focus of the scan transfer device, and the scan transfer device is adapted to be positioned so that the pupillary point of the eye is accommodated at the second focus of the scan transfer device.

2. An apparatus according to claim 1, wherein the illuminating device is configured to illuminate the retina by scanning collimated light across the retina of the eye in one dimension.

3. An apparatus according to claim 2, wherein the axis of rotation of the illuminating device lies on a plane defined by the one-dimensional scan produced by the illuminating device.

4. An apparatus according to claim 1, wherein the illuminating device comprises:
   a source of collimated light; and
   a scanning element,
   wherein the source of collimated light and the scanning element combine to provide a one-dimensional collimated light scan from the first point and
   wherein the scan transfer device transfers the one-dimensional collimated light scan from the first point into the eye.

5. The apparatus according to claim 4, wherein the scanning element is one of the group consisting of an oscillating mechanism, an oscillating mirror, a resonant scanner, a resonant scanning mirror and a microelectromechanical system (MEMS) scanning element.

6. The apparatus according to claim 1, wherein the light source includes one or more light sources of differing wavelengths.

7. The apparatus according to claim 1, wherein the light source is located with the illuminating device, such that it rotates with the illuminating device.

8. The apparatus according to claim 1, wherein the apparatus further comprises one or more detectors for detecting the reflected light from the retina to produce an image of the retina.

9. The apparatus according to claim 8, wherein the one or more detectors are located with the illuminating device, such that they rotate with the illuminating device.

10. The apparatus according to claim 9, wherein the one or more detectors are configured to obtain a substantially one-dimensional image of the retina from the circumferential line illuminated by the light.

11. The apparatus according to claim 10, wherein the illuminating device comprises:
    a scanning element,
    wherein the source of collimated light and the scanning element combine to provide a one-dimensional collimated light scan from the first point, and
    wherein the scan transfer device transfers the one-dimensional collimated light scan from the first point into the eye.

12. The apparatus according to claim 11, wherein the scanning element is one of the group consisting of an oscillating mechanism, an oscillating mirror, a resonant scanner, a resonant scanning mirror and a microelectromechanical system (MEMS) scanning element.

13. The apparatus according to claim 11, wherein the light source includes one or more light sources of differing wavelengths.

14. The apparatus according claim 11, wherein the light source is located with the imaging device, such that it rotates with the imaging device.

15. The apparatus according to claim 8, wherein the one or more detectors are configured to obtain a substantially one-dimensional image of the retina from the circumferential line illuminated by the light.

16. The apparatus according to claim 15, wherein the illuminating device comprises:
    a scanning element,
    wherein the source of collimated light and the scanning element combine to provide a one-dimensional collimated light scan from the first point, and
    wherein the scan transfer device transfers the one-dimensional collimated light scan from the first point into the eye.

17. The apparatus according to claim 16, wherein the scanning element is one of the group consisting of an oscillating mechanism, an oscillating mirror, a resonant scanner, a resonant scanning mirror and a microelectromechanical system (MEMS) scanning element.

18. The apparatus according to claim 16, wherein the light source includes one or more light sources of differing wavelengths.

19. The apparatus according claim 16, wherein the light source is located with the imaging device, such that it rotates with the imaging device.

20. The apparatus according claim 16, wherein the light output by the light source is transmitted to the light source from a further light source located remotely from the imaging device.

21. The apparatus according to claim 1, wherein the light output by the light source is transmitted to the light source from a further light source located remotely from the illuminating device.

22. A method of illuminating the retina of an eye with collimated light comprising the steps of:
    providing an illuminating device including a light source capable of producing light in a plane, the light radiating in said plane from a first point such that, in use, the illuminating device illuminates a circumferential line on the retina lying on said plane;
    providing a support structure, wherein the illuminating device is pivotably mountable to the support structure and is automatically rotatable about an axis which lies substantially on the plane defined by the light source and which extends through a second point;

providing a scan transfer device having first and second foci, the first point being provided at the first focus of the scan transfer device and the second point being provided at the second focus of the scan transfer device;

positioning the scan transfer device so that the pupillary point of the eye is accommodated at the second focus of the scan transfer device; and automatically rotating the illuminating device about the axis to illuminate a plurality of circumferential lines on the retina with collimated light by scanning the circumferential line illuminated by the light about said axis.

23. A method of imaging the retina of an eye using collimated light comprising the steps of:

providing an illuminating device including a light source capable of producing light in a plane, the light radiating in said plane from a first point such that, in use, the illuminating device illuminates a circumferential line on the retina lying on said plane and centered on a second point, the illuminating device further comprising a scan transfer device, wherein the scan transfer device has first and second foci, the first point is provided at the first focus of the scan transfer device, the second point is provided at the second focus of the scan transfer device, and the scan transfer device is adapted to be positioned so that the pupillary point of the eye is accommodated at the second focus of the scan transfer device;

providing one or more detectors for detecting the reflected light from the retina to produce an image of the retina;

providing a support structure, wherein the illuminating device is pivotably mountable to the support structure and is rotatable about an axis which lies substantially on the plane defined by the light source and which extends through said second point; and rotating the illuminating device about the axis to illuminate a plurality of circumferential lines on the retina with collimated light and to obtain a plurality of substantially one-dimensional images of the retina by scanning the circumferential line illuminated by the light about said axis; and combining the plurality of substantially one-dimensional images to obtain a two-dimensional image of the retina.

24. The method according to claim 23, wherein the one or more detectors are located with the illuminating device, such that they rotate with the illuminating device.

* * * * *